United States Patent [19]

Aristoff

[11] Patent Number: 4,486,598
[45] Date of Patent: * Dec. 4, 1984

[54] CARBACYCLIN ANALOGS

[75] Inventor: Paul A. Aristoff, Portage, Mich.

[73] Assignee: The Upjohn Company, Kalamazoo, Mich.

[*] Notice: The portion of the term of this patent subsequent to Dec. 15, 1998 has been disclaimed.

[21] Appl. No.: 351,069

[22] Filed: Feb. 22, 1982

[51] Int. Cl.³ .................. C07C 177/00; A61K 31/557
[52] U.S. Cl. .................................. 562/466; 568/807; 568/808; 560/56; 424/308; 424/317; 560/28; 562/451; 562/452; 562/455; 260/239 BF; 260/465 F; 260/465 D; 544/154; 544/171; 544/176; 544/336; 544/386; 546/203; 546/205; 546/285; 546/309; 546/314; 546/337; 548/280; 548/528; 564/80; 564/88; 564/90; 564/95; 564/172; 564/174; 564/158; 568/632; 568/633; 568/634; 568/734
[58] Field of Search ............... 560/56, 28; 562/451, 562/452, 455, 239 BF, 466; 260/465 F, 465 D; 544/154, 171, 176, 336, 386; 546/203, 205, 285, 314, 309, 337; 548/280, 528; 564/80, 172, 174, 88, 90, 95, 158; 568/632, 633, 634, 734, 807, 808

[56] References Cited

U.S. PATENT DOCUMENTS

| | | | |
|---|---|---|---|
| 4,180,657 | 12/1979 | Sih | 542/426 |
| 4,192,891 | 3/1980 | Haslanger | 424/305 |
| 4,225,508 | 9/1980 | Sih | 260/346.22 |
| 4,238,414 | 12/1980 | Morton, Jr. | 564/453 |
| 4,306,075 | 12/1981 | Aristoff | 560/56 |
| 4,306,076 | 12/1981 | Nelson | 560/56 |

FOREIGN PATENT DOCUMENTS

| | | |
|---|---|---|
| 2900352 | 7/1979 | Fed. Rep. of Germany . |
| 4024865 | 2/1979 | Japan . |
| 4063059 | 5/1979 | Japan . |
| 4063060 | 5/1979 | Japan . |
| 2012265 | 7/1979 | United Kingdom . |
| 2013661 | 8/1979 | United Kingdom . |
| 2017699 | 10/1979 | United Kingdom . |

OTHER PUBLICATIONS

Aristoff, P. A., J. Org. Chem. 46 (No. 9), 1981, pp. 1954–1957 "Practical Synthesis of 6a-Carbaprostaglandin I₂".
Barco, A., et al., J. Org. Chem. 45 (No. 23), 1980, pp. 4776–4778 "A New Elegant Route to a Key Intermediate for the Synthesis of 9(O)-Methanoprostacyclin".
Hayashi, M., et al., Chem. Lett. 1979, pp. 1437–1440 "A Synthesis of 9(O)-Methanoprostacyclin".
Kojima, K., et al., Tetrahedron Lett. 39, 1978, pp. 3743–3746 "Total Synthesis of 9(O)-Methanoprostacyclin and Its Isomers".
Morton, D. R., Jr., et al., J. Org. Chem. 44 (No. 16), 1979, pp. 2880–2887 "Total Synthesis of 6a-Carbaprostaglandin I₂ and Related Isomers".
Nicolaou, K. C., et al., J.C.S. Chem. Comm., 1978, pp. 1067–1068 "Total Synthesis of Carboprostacyclin, a Stable and Biologically Active Analogue of Prostacyclin(PGI₂)".
Shibasaki, M., et al., Chem. Lett. 1979, pp. 1299–1300 "A Stereo and Regiospecific Route to the Synthetic Intermediate for the Synthesis of 9(O)-Methanoprostacyclin".
Shibasaki, M., et al., Tetrahedron Lett. 5, 1979, pp. 433–436 "New Synthetic Routes to 9(O)-Methanoprostacyclin, A Highly Stable and Biologically Potent Analog of Prostacyclin".
Skuballa, W., et al., Angew. Chem. 93 (No. 12), 1981, pp. 1080–1081 "Ein neuer Weg zu 6a-Carbacyclinen-Synthese eines stabilen, biologisch potenten Prostacyclin-Analogons".
Sugie, A., et al., Tetrahedron Lett. 28, 1979, pp. 2607–2610 "Stereocontrolled Approaches to 9(O)-Methanoprostacyclin".
Yamazaki, M., et al., Chem. Lett. 1981, pp. 1245–1248 "1,2-Carbonyl Transposition of cis-Bicyclo[3.3.0]octan-2-one to Its 3-one Skeleton: Application to Syntheses of dl-Hirsutic Acid and dl-9(O)-Methanoprostacyclin".

Primary Examiner—Robert Gerstl
Attorney, Agent, or Firm—L. Ruth Hattan

[57] ABSTRACT

Novel compounds of the following general formula:

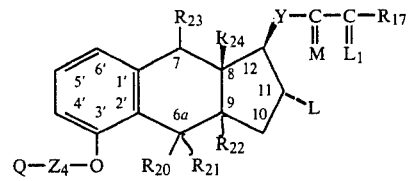

7 Claims, No Drawings

CARBACYCLIN ANALOGS

BACKGROUND OF THE INVENTION

The present invention relates to novel compounds which are carbacyclin analogs, to processes for the preparation of said carbacyclin analogs and the use of said analogs as pharmacological agents or as intermediates for the preparation of compounds useful as pharmacological agents. This invention also relates to chemical intermediates for preparing the novel carbacyclin compounds described and claimed herein.

Prostacyclin is an endogenously produced compound in mammalian species, being structurally and biosynthetically related to the prostaglandins (PG's). In particular, prostacyclin exhibits the structure and carbon atom numbering of formula I when the C-5,6 positions are unsaturated. For convenience, prostacyclin is often referred to simply as "$PGI_2$". Carbacyclin, 6a-carba-$PGI_2$, exhibits the structure and carbon atom numbering indicated in formula II when the C-5,6 positions are unsaturated. Likewise, for convenience, carbacyclin is referred to simply as "$CBA_2$".

A stable partially saturated derivative of $PGI_2$ is $PGI_1$ or 5,6-dihydro-$PGI_2$ when the C-5,6 positions are saturated, depicted with carbon atom numbering in formula I when the C-5,6 positions are saturated. The corresponding 5,6-dihydro-$CBA_2$ is $CBA_1$, depicted in formula II when the C-5,6 positions are saturated.

As is apparent from inspection of formulas I and II, prostacyclin and carbacyclin may be trivially named as derivatives of PGF-type compounds, e.g., $PGF_2\alpha$ of formula III. Accordingly, prostacyclin is trivially named 9-deoxy-6,9α-epoxy-(5Z)-5,6-didehydro-$PGF_1$ and carbacyclin is named 9-deoxy-6,9α-methano-(5Z)-5,6-didehydro-$PGF_1$. For description of prostacyclin and its structural identification, see Johnson, et al, Prostaglandins 12:915 (1976).

In naming the novel compounds of the present invention in general the art-recognized system of nomenclature described by N. A. Nelson, J. Med. Chem. 17:911 (1974) for prostaglandins is followed. As a matter of convenience, however, the novel carbacyclin derivatives herein are named as 6a-carba-prostaglandin $I_2$ compounds, or as $CBA_1$ or $CBA_2$ derivatives.

In the formulas herein, broken line attachments to a ring indicate substituents in the "alpha" (α) configuration, i.e., below the plane of said ring. Heavy solid line attachments to a ring indicate substituents in the "beta" (β) configuration, i.e., above the plane of said ring. The use of wavy lines (∼) herein will represent attachment of substituents in the alpha or beta configuration or attached in a mixture of alpha and beta configurations. Alternatively wavy lines will represent either an E or Z geometric isomeric configuration or the mixture thereof. Also, solid and dotted lines used together, as for example, in formulas I and II at C-5,6 positions indicates the presence of either a double bond or alternatively a single bond.

A side chain hydroxy at C-15 in the formulas herein is in the S or R configuration as determined by the Cahn-Ingold-Prelog sequence rules, J. Chem. Ed. 41:16 (1964). See also Nature 212:38 (1966) for discussion of the stereochemistry of the prostaglandins which discussion applies to the novel carbacyclin analogs herein. Molecules of carbacyclin have several centers of asymmetry and therefore can exist in optically inactive form or in either of two enantiomeric (optically active) forms, i.e., the dextrorotatory and laveorotatory forms. The racemic form of carbacyclin contains equal numbers of both enantiomeric molecules. For convenience, reference to carbacyclin or $CBA_2$ or $CBA_1$ will refer to the optically active form thereof.

A formula as drawn herein which depicts a prostacyclin-type product or an intermediate useful in the preparation thereof, represents that particular stereoisomer of the prostacyclin-type product which is of the same relative stereochemical configuration as prostacyclin obtained from mammalian tissues or the particular stereoisomer of the intermediate which is useful in preparing the above stereoisomer of the prostacyclin type product. As drawn, formula I corresponds to that of $PGI_2$ endogenously produced in the mammalian species. In particular, refer to the stereochemical configuration at C-8 (α), C-9 (α), C-11 (α) and C-12 (β) of endogenously produced prostacyclin. The mirror image of the above formula for prostacyclin represents the other enantiomer.

The term "prostacyclin analog" or "carbacyclin analog" represents that stereoisomer of a prostacyclin-type product which is of the same relative stereochemical configuration as prostacyclin obtained from mammalian tissues or a mixture comprising stereoisomer and the enantiomers thereof. In particular, where a formula is used to depict a prostacyclin type product herein, the term "prostacyclin analog" or "carbacyclin analog" refers to the compound of that formula or a mixture comprising that compound and the enantiomer thereof.

PRIOR ART

Carbacyclin and closely related compounds are known in the art. See Japanese Kokia 63,059 and 63,060, also abstracted respectively as Derwent Farmdoc CPI Numbers 48154B/26 and 48155B/26. See also British published specifications 2,012,265 and German Offenlungsschrift 2,900,352, abstracted as Derwent Farmdoc CPI Number 54825B/30. See also British published applications 2,017,699 and 2,013,661 and U.S. Pat. No. 4,238,414.

The synthesis of carbacyclin and related compounds is also reported in the chemical literature, as follows: Morton, D.R., et al, J. Org. Chem., 44:2880-2887 (1979); Shibasaki, M., et al, Tetrahedron Lett., 433-436 (1979); Kojima, K., et al, Tetrahedron Lett., 3743-3746 (1978); Nicolaou, K. C., et al, J. Chem. Soc., Chemical Communications, 1067-1068 (1978); Sugie, A., et al, Tetrahedron Lett., 2607-2610 (1979); Shibasaki, M., Chem. Lett., 1299-1300 (1979), and Hayashi, M., Chem. Lett., 1437-40 (1979); Aristoff, P. A., J. Org. Chem. 46, 1954-1957(1981); Yamazaki, M., et al, Chem. Lett., 1245-1248(1981); and Barco, A., et al, J. Org. Chem. 45, 4776-4778(1980); and Skuballa, W., et al, Angew. Chem. 93, 1080-1081 (1981).

7-Oxo and 7-hydroxy-$CBA_2$ compounds are apparently disclosed in U.S. Pat. No. 4,192,891. 19-Hydroxy-$CBA_2$ compounds are disclosed in U.S. Pat. No. 4,225,508. $CBA_2$ aromatic esters are disclosed in U.S. Pat. No. 4,180,657. 11-Deoxy-$\Delta^{10}$- or $\Delta^{11}$-$CBA_2$ compounds are described in Japanese Kokai No. 77/24,865, published 24 Feb. 1979. Related benzindene compounds are disclosed in U.S. Pat. Nos. 4,306,075 and 4,306,076.

SUMMARY OF THE INVENTION

The present invention consists of compounds of formula IV wherein Q is (1) —COOR₅, wherein R₅ is
  (a) hydrogen,
  (b) $(C_1-C_{12})$alkyl,
  (c) $(C_3-C_{10})$cycloalkyl,
  (d) $(C_7-C_{12})$aralkyl,
  (e) phenyl optionally substituted with one, 2 or 3 chloro or $(C_1-C_4)$alkyl,
  (f) phenyl substituted in the para-position with —NHCOR₆, —COR₇, —OC(O)R₈ or —CH=N—NHCONH₂, wherein R₆ is methyl, phenyl, acetamidophenyl, benzamidophenyl or —NH₂; R₇ is methyl, phenyl, —NH₂, or methoxy; and R₈ is phenyl or acetamidophenyl;
  (g) phthalidyl,
  (h) 3-(5,5-dimethyl-1,3,2-dioxaphosphorinan-2-yl)-2-oxopropan-1-yl P-oxide,
  (i) 3-(5,5-di(hydroxymethyl)-1,3,2-dioxaphosphorinan-2-yl)-2-oxopropan-1-yl P-oxide, or
  (j) a pharmacologically acceptable cation;
(2) —CH₂OH;
(3) —COL₂, wherein L₂ is
  (a) an amino group of the formula —NR₉R₁₀ wherein R₉ is hydrogen or $(C_1-C_{12})$alkyl and R₁₀ is
    (i) hydrogen
    (ii) $(C_1-C_{12})$alkyl
    (iii) $(C_3-C_{10})$cycloalkyl,
    (iv) $(C_7-C_{12})$aralkyl
    (v) phenyl optionally substituted with one, 2 or 3 chloro, $(C_1-C_3)$alkyl, hydroxy, carboxy, $(C_2-C_5)$alkoxycarbonyl, or nitro,
    (vi) $(C_2-C_5)$carboxyalkyl,
    (vii) $(C_2-C_5)$carbamoylalkyl,
    (viii) $(C_2-C_5)$cyanoalkyl,
    (ix) $(C_3-C_6)$acetylalkyl,
    (x) $(C_7-C_{12})$benzoalkyl, optionally substituted by one, 2, or 3 chloro, $(C_1-C_3)$alkyl, hydroxy, $(C_1-C_3)$alkoxy, carboxy, $(C_2-C_5)$-alkoxycarbonyl, or nitro,
    (ix) pyridyl, optionally substituted by one, 2, or 3 chloro, $(C_1-C_3)$alkyl, or $(C_1-C_3)$alkoxy,
    (xii) $(C_6-C_9)$pyridylalkyl optionally substituted by one, 2, or 3 chloro, $(C_1-C_3)$alkyl, hydroxy, or $(C_1-C_3)$alkyl,
    (xiii) $(C_1-C_4)$hydroxyalkyl,
    (xiv) $(C_1-C_4)$dihydroxyalkyl,
    (xv) $(C_1-C_4)$trihydroxyalkyl;
  (b) cycloamine selected from the group consisting of pyrolidino, piperidino, morpholino, piperazino, hexamethyleneimino, pyrroline, or 3,4-didehydropiperidinyl optionally substituted by one or 2 $(C_1-C_{12})$alkyl;
  (c) carbonylamino of the formula —NR₁₁COR₁₀, wherein R₁₁ is hydrogen or $(C_1-C_4)$alkyl and R₁₀ is other than hydrogen, but otherwise defined as above;
  (d) sulfonylamino of the formula —NR₁₁SO₂R₁₀, wherein R₁₁ and R₁₀ are defined in (c);
(4) —CH₂NL₃L₄, wherein L₃ and L₄ are hydrogen or $(C_1-C_4)$ alkyl, being the same or different, or the pharmacologically acceptable acid addition salts thereof when Q is —CH₂NL₃L₄; or
(5) —CN;
wherein Z₄ is —CH₂— or —(CH₂)_f—CF₂— wherein f is zero, one, 2 or 3;
wherein
(1) each of R₂₀, R₂₁, R₂₂, R₂₃ and R₂₄ is hydrogen with R₂₂ being either α-hydrogen or β-hydrogen;

(2) R₂₀ is hydrogen, R₂₁ and R₂₂ taken together form a second valence bond between C-9 and C-6a, and R₂₃ and R₂₄ taken together form a second valence bond between C-7 and C-8 or both R₂₃ and R₂₄ are hydrogen.
(3) each of R₂₂, R₂₃ and R₂₄ is hydrogen with R₂₂ being either α-hydrogen or β-hydrogen, and
  (a) R₂₀ and R₂₁ taken together are oxo, or
  (b) R₂₀ is hydrogen and R₂₁ is hydroxy, being α-hydroxy or β-hydroxy;
wherein L is H,H; α-OH₁₂,β-H; α-H,β-OH₁₂; α-CH₂OH,β-H; α-H,β-CH₂OH;
wherein Y is trans —CH=CH—, cis—CH=CH—, —CH₂CH₂—, or —C≡C—;
wherein M is α-OH,β-R₁₄ or α-R₁₄,β-OH; wherein R₁₄ is hydrogen or methyl;
wherein L₁ is α-R₁₅,βR₁₆; α-R₁₆,β-R₁₅; or a mixture thereof wherein R₁₅ and R₁₆ are hydrogen, methyl, or fluoro being the same or different with the proviso that one of R₁₅ and R₁₆ is fluoro only when the other of R₁₅ and R₁₆ is hydrogen or fluoro;
wherein R₁₇ is

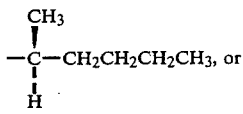

wherein 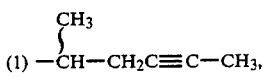 taken together is

CH₃
    |
(1) —CH—CH₂C≡C—CH₃, (2) —C≡C—C_qH_{2q}CH₃ wherein q is an integer of from 2 to 6, or
(3) —C_pH_{2p}CH=CH₂ wherein p is an integer of from 3 to 7;
and individual optical isomers thereof.

In the compounds of the present invention, and as used herein, ( - - - ) denotes the α-configuration, ( — ) denotes the β-configuration, (~) denotes α- and/or β-configuration or the E and/or Z isomer.

With regard to the divalent groups described above, i.e., M, L and L₁ said divalent groups are defined in terms of an α-substituent and a β-substituent which means that the α-substituent of the divalent group is in the alpha configuration with respect to the plane of the C-8 to C-12 cyclopentane ring and the β-substituent is in the beta configuration with respect to said cyclopentane ring.

The carbon atom content of various hydrocarbon containing groups is indicated by a prefix designating the minimum and maximum number of carbon atoms in the moiety. For example, in defining the moiety L₂ in the —COL₂ substituent group the definition $(C_1-C_{12})$alkyl means that L₂ can be an alkyl group having from one to 12 carbon atoms. Additionally, any moiety so defined includes straight chain or branched chain groups. Thus $(C_1-C_{12})$alkyl as set forth above includes straight or branched chain alkyl groups having from 1 to 12 carbon atoms and as additional illustration, when L₂ represents, for example, $(C_2-C_5)$carboxyalkyl, the alkyl moiety thereof contains from 1 to 4 carbon atoms and is a straight chain or a branched chain alkyl group.

The formula IV CBA analogs wherein $R_{20}$, $R_{21}$, $R_{22}$, $R_{23}$, and $R_{24}$ are all hydrogen with $R_{22}$ being β-hydrogen are characterized as "9-deoxy-2',9α-methano-3-oxa-4,5,6-trinor-3,7-(1',3'-inter-phenylene)-PGF$_1$" compounds. Corresponding compounds wherein $R_{22}$ is α-hydrogen are characterized as "9-deoxy-2',9β-methano-3-oxa-4,5,6-trinor-3,7-(1',3'-inter-phenylene)-PGF$_1$" compounds. The formula IV compounds wherein $R_{20}$, $R_{23}$, and $R_{24}$ are all hydrogen and $R_{21}$ and $R_{22}$ taken together form a valence bond between C-9 and C-6a are characterized as "9-deoxo-2',9-metheno-3-oxo-3,4,5-trinor-3,7-(1',3'-inter-phenylene)-PGF$_1$" compounds. The formula IV compounds wherein $R_{20}$ is hydrogen and $R_{21}$ and $R_{22}$ taken together form a second valence bond between C-9 and C-6a and $R_{23}$ and $R_{24}$ taken together form a second valence bond between C-7 and C-8 are characterized as "9-deoxo-2',9-metheno-3-oxa-3,4,5-trinor-3,7-(1',3'-inter-phenylene)-7,8-didehydro-PGE$_1$" compounds. The formula IV compounds wherein $R_{22}$, $R_{23}$, and $R_{24}$ are all hydrogen and $R_{20}$ and $R_{21}$ taken together are oxo are characterized as "6a-oxo-9-deoxy-2'9α-methano-3-oxa-4,5,6-trinor-3,7-(1',3'-inter-phenylene)-PGF$_1$" or "6a-oxo-9-deoxy-2',9β-methano-3-oxa-4,5,6-trinor-3,7-(1',3'-inter-phenylene)-PGF$_1$" depending on whether $R_{22}$ is α-hydrogen or β-hydrogen, respectively. Formula IV compounds wherein $R_{20}$, $R_{22}$, $R_{23}$, and $R_{24}$ are all hydrogen and $R_{21}$ is α-hydroxy are characterized as "6aα-hydroxy-9-deoxy-2',9α-methano-3-oxa-4,5,6-trinor-3,7-(1',3'-inter-phenylene)-PGF$_1$" or "6aα-hydroxy-9-deoxy-2',9β-methano-3-oxa-4,5,6-trinor-3,7-(1',3'-inter-phenylene)-PGF$_1$ compounds depending on whether $R_{22}$ is α-hydrogen or β-hydrogen, respectively. Finally, formula IV compounds where $R_{20}$, $R_{22}$, $R_{23}$, and $R_{24}$ are all hydrogen and $R_{21}$ is β-hydroxy are characterized as "6aβ-hydroxy-9deoxy-2',9β-methano-3-oxa-4,5,6-trinor-3,7-(1',3'-inter-phenylene)-PGF$_1$" or "6aβ-hydroxy-9-deoxy-2',9α-methano-3-oxa-4,5,6-trinor-3,7-(1',3'-inter-phenylene)-PGF$_1$" compounds depending on whether $R_{22}$ is α-hydrogen or b-hydrogen, respectively. When $Z_4$ is $-(CH_2)_f-CF_2-$ and f is zero, the formula IV compounds are additionally characterized as "2,2-difluoro" compounds. When f is one, 2, or 3, such compounds are additionally characterized as "2a-homo", "2a,2b-dihomo" or "2a,2b,2c-trihomo" compounds.

When $R_{14}$ is methyl, the carbacyclin analogs are all named as "15-methyl-" compounds. Further, except for compounds wherein Y is cis—CH=CH—, compounds wherein the M moiety contains an hydroxyl in the beta configuration are additionally named as "15-epi-" compounds.

For the compounds wherein Y is cis—CH=CH—, then compounds wherein the M moiety contains an hydroxyl in the alpha configuration are named as "15-epi-CBA" compounds. For a description of this convention of nomenclature for identifying C-15 epimers, see U.S. Pat. No. 4,016,184, issued 5 Apr. 1977, particularly columns 24–27 thereof.

The compounds of the present invention which contain $-(CH_2)_2-$, cis—CH=CH—, or $-C\equiv C-$ as the Y moiety, are accordingly referred to as "13,14-dihydro", "cis-13", or "13,14-didehydro" compounds, respectively.

When $R_{17}$ is

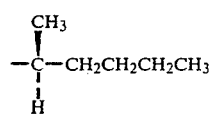

the compounds so described are named as 17(S),20-dimethyl compounds.

When $-C(L_1)-R_{17}$ is

the compounds are named as "16-(R,S)methyl-18,19-tetradehydro" compounds.

When $-C(L_1)R_{17}$ is $-C\equiv C-C_qH_{2q}CH_3$ wherein q is an integer of from 2 to 6 the compounds so described are named as "16,17-tetrahydro", "16,17-tetradehydro-20-methyl", "16,17-tetradehydro-20-ethyl", "16,17-tetrahydro-20-n-propyl" and "16,17-tetrahydro-20-n-butyl" compounds as the integer as represented by q varies from 2 to 6 respectively.

When $-C(L_1)R_{17}$ is $-C_pH_{2p}CH=CH_2$ wherein p is an integer of from 3 to 7 the compounds so described are named as "19,20-didehydro", "19,20-didehydro-18a,18b-dihomo", "19,20-didehydro-18a,18b,18c-trihomo", "19,20-didehydro-18a,18b,18c,18d-tetrahomo" compounds as the integer represented by p varies from 3 to 7 respectively.

When at least one of $R_{15}$ and $R_{16}$ is not hydrogen then there are described the "16-methyl" (one and only one of $R_{15}$ and $R_{16}$ is methyl), "16,16-dimethyl" ($R_{15}$ and $R_{16}$ are both methyl), "16-fluoro" (one and only one of $R_{15}$ and $R_{16}$ is fluoro), "16,16-difluoro" ($R_{15}$ and $R_{16}$ are both fluoro) compounds. For those compounds wherein $R_{15}$ and $R_{16}$ are different, the carbacyclin analogs so represented contain an asymmetric carbon atom at C-16. Accordingly, two epimeric configurations are possible: "(16S)" and "(16R)". Further, there is described by this invention the C-16 epimeric mixture: "(16RS)".

When Q is $-CH_2OH$, the compounds so described are named as "2-decarboxy-2-hydroxymethyl" compounds.

When Q is $-CH_2NL_3L_4$, the compounds so described are named as "2-decarboxy -2-aminomethyl" or "2-(substituted amino)methyl compounds.

When Q is $-COL_2$, the novel compounds herein are named as amides. Further, when Q is $-COOR_5$ and $R_5$ is other than hydrogen the novel compounds herein are named as esters and salts.

When Q is CN the novel compounds herein are named as 2-decarboxy-2-cyano compounds.

Examples of phenyl esters substituted in the para position (i.e., Q is $-COOR_5$, $R_5$ is p-substituted phenyl) include p-acetamidophenyl ester, p-benzamidophenyl ester, p-(p-acetamidobenzamido)phenyl ester, p-(p-benzamidobenzamido)phenyl ester, p-amidocarbonylaminophenyl ester, p-acetylphenyl ester, p-benzoylphenyl ester, p-aminocarbonylphenyl ester, p-methoxycarbonylphenyl ester, p-benzoyloxyphenyl ester, p-(p-acetamidobenzoyloxy)phenyl ester, and p-hydroxybenzaldehyde semicarbazone ester.

Examples of novel amides herein (i.e., Q is $-COL_2$) include the following.

(1) Amides within the scope of alkylamino groups of the formula-$NR_9R_{10}$ are methylamide, ethylamide, n-propylamide, isopropylamide, n-butylamide, n-pentylamide, tert-butylamide, neopentylamide, n-hexylamide, n-heptylamide, n-octylamide, n-nonylamide, n-decylamide, n-undecylamide, and n-dodecylamide, and isomeric forms thereof. Further examples are dimethylamide, diethylamide, di-n-propylamide, diisopropylamide, di-n-butylamide, methylethylamide, di-tert-butylamide, methylpropylamide, methylbutylamide, ethylpropylamide, ethylbutylamide, and propylbutylamide. Amides within the scope of cycloalkylamino are cyclopropylamide, cyclobutylamide, cyclopentylamide, 2,3-dimethylcyclopentylamide, 2,2-dimethylcyclopentylamide, 2-methylcyclopentylamide, 3-tert-butylcyclopentylamide, cyclohexylamide, 4-tert-butylcyclohexylamide, 3-isopropylcyclohexylamide, 2,2-dimethylcyclohexylamide, cycloheptylamide, cyclooctylamide, cyclononylamide, cyclodecylamide, N-methyl-N-cyclobutylamide, N-methyl-N-cyclopentylamide, N-methyl-N-cyclohexylamide, N-ethyl-N-cyclopentylamide, and N-ethyl-N-cyclohexylamide. Amides within the scope of aralkylamino are benzylamide, 2-phenylethylamide, and N-methyl-N benzyl-amide. Amides within the scope of substituted phenylamide are p-chloroanilide, m-chloroanilide, 2,4-dichloroanilide, 2,4,6-trichloroanilide, m-nitroanilide, p-nitroanilide, p-methoxyanilide, 3,4-dimethoxyanilide, 3,4,5-trimethoxyanilide, p-hydroxymethylanilide, p-methylanilide, m-methyl anilide, p-ethylanilide, t-butylanilide, p-carboxyanilide, p-methoxycarbonyl anilide, p-carboxyanilide and o-hydroxyanilide. Amides within the scope of carboxyalkylamino are carboxyethylamide, carboxypropylamide and carboxymethylamide, carboxybutylamide. Amides within the scope of carbamoylalkylamino are carbamoylmethylamide, carbamoylethylamide, carbamoylpropylamide, and carbamoylbutylamide. Amides within the scope of cyanoalkylamino are cyanomethylamide, cyanoethylamide, cyanopropylamide, and cyanobutylamide. Amides within the scope of acetylalkylamino are acetylmethylamide, acetylethylamide, acetylpropylamide, and acetylbutylamide. Amides within the scope of benzoylalkylamino are benzoylmethylamide, benzoylethylamide, benzoylpropylamide, and benzoylbutylamide. Amides within the scope of substituted benzoylalkylamino are p-chlorobenzoylmethylamide, m-chlorobenzoylmethylamide, 2,4-dichlorobenzoylmethylamide, 2,4,6-trichlorobenzoylmethylamide, m-nitrobenzoylmethylamide, p-nitrobenzoylmethylamide, p-methoxybenzoylmethylamide, 2,4-dimethoxy benzoylmethylamide, 3,4,5-trimethoxybenzoylmethylamide, p-hydroxymethylbenzoylmethylamide, p-methylbenzoylmethylamide, m-methylbenzoylmethylamide, p-ethylbenzoylmethylamide, t-butylbenzoylmethylamide, p-carboxybenzoylmethylamide, m-methoxycarbonylbenzoylmethylamide, o-carboxybenzoylmethylamide, o-hydroxybenzoylmethylamide, p-chlorobenzoylethylamide, m-chlorobenzoylethylamide, 2,4-dichlorobenzoylethylamide, 2,4,6-trichlorobenzoylethylamide, m-nitrobenzoylethylamide, p-nitrobenzoylethylamide, p-methoxybenzoylethylamide, p-methoxybenzoylethylamide, 2,4-dimethoxybenzoylethylamide, 3,4,5trimethoxybenzoylethylamide, p-hydroxymethylbenzoylethylamide, p-methylbenzoylethylamide, m-methylbenzoylethylamide, p-ethylbenzoylethylamide, t-butylbenzoylethylamide, p-carboxybenzoylethylamide, m-methoxycarbonylbenzoylethylamide, o-carboxybenzoylethylamide, o-hydroxybenzoylethylamide, p-chlorobenzoylpropylamide, m-chlorobenzoylpropylamide, 2,4-dichlorobenzoylpropylamide, 2,4,6-trichlorobenzoylpropylamide, m-nitrobenzoylpropylamide, p-nitrobenzoylpropylamide, p-methoxybenzoylpropylamide, 2,4-dimethoxybenzoylpropylamide, 3,4,5-trimethoxybenzoylpropylamide, p-hydroxymethylbenzoylpropylamide, p-methylbenzoylpropylamide, m-methylbenzoylpropylamide, p-ethylbenzoylpropylamide, t-butylbenzoylpropylamide, p-carboxybenzoylpropylamide, m-methoxycarbonylbenzoylpropylamide, o-carboxybenzoylpropylamide, o-hydroxybenzoylpropylamide, p-chlorobenzoylbutylamide, m-chlorobenzoylbutylamide, 2,4-dichlorobenzoylbutylamide, 2,4,6-trichlorobenzoylbutylamide, m-nitrobenzoylmethylamide, p-nitrobenzoylbutylamide, p-methoxybenzoylbutylamide, 2,4-dimethoxybenzoylbutylamide, 3,4,5-trimethoxybenzoylbutylamide, p-hydroxymethylbenzoylbutylamide, p-methylbenzoylbutyamide, m-methylbenzoylbutylamide, p-ethylbenzoylbutyalmide, m-methylbenzoylbutylamide, p-ethylbenzoylbutylamide, t-butylbenzoylbutylamide, p-carboxybenzoylbutylamide, m-methoxycarbonylbenzoylbutylamide, o-carboxybenzoylbutylamide, o-hydroxybenzoylmethylamide. Amides within the scope of pyridylamino are α-pyridylamide, β-pyridylamide, and γ-pyridylamide. Amides within the scope of substituted pyridylamino are 4-methyl-α-pyridylamide, 4methyl-β-pyridylamide, 4-chloro-α-pyridylamide, and 4-chloro-β-pyridylamide. Amides within the scope of pyridylalkylamino are α-pyridylmethylamide, β-pyridylmethylamide, γ-pyridylmethylamide, α-pyridylethylamide, β-pyridylethylamide, γ-pyridylethylamide, α-pyridylpropylamide, β-pyridylpropylamide, γ-pyridylpropylamide, α-pyridylbutylamide, β-pyridylbutylamide, and γ-pyridylbutylamide. Amides within the scope of substituted pyridylalkylamido are 4-methyl-α-pyridylmethylamide, 4-methyl-β-pyridylmethylamide, 4-chloro-α-pyridylmethylamide, 4-chloro-β-pyridylmethyl-amide, 4-methyl-α-pyridylpropylamide, 4-methyl-β-pyridylpropylamide, 4-chloro-α-pyridylpropylamide, 4-chloro-β-pyridylpropylamide, 4-methyl-α-pyridylbutylamide, 4-methyl-β-pyridylbutylamide, 4-chloro-α-pyridylbutylamide, 4-chloro-β-pyridylbutylamide, 4-chloro-γ-pyridylbutylamide. Amides within the scope of hydroxyalkylamino are hydroxymethylamide, β-hydroxyethylamide, β-hydroxypropylamide, γ-hydroxypropylamide, 1-(hydroxymethyl)ethyl-amide, 1-(hydroxymethyl)propylamide, (2-hydroxymethyl)propylamide, and α,α,-dimethyl-hydroxyethylamide. Amides within the scope of dihydroxyalkylamino are dihydroxymethylamide, β,γ-dihydroxypropylamide, 1-(hydroxymethyl)2-hydroxymethylamide, β,γ-dihydroxybutylamide, β,δ-dihydroxybutyl-amide, γ,δ-dihydroxybutylamide, and 1,1-bis(hydroxymethyl)ethylamide. Amides within the scope of trihydroxyalkylamino are tris(hydroxymethyl)methylamide and 1,3-dihydroxy-2-hydroxymethylpropylamide.

(2) Amides within the scope of cycloamino groups described above are pyrrolidylamide, piperidylamide, morpholinylamide, hexamethyleneiminylamide, piperazinylamide, pyrrolinylamide, and 3,4-didehydropiperidinylamide each of which may be optionally substituted with one or 2 straight or branched alkyl chains having from 1 to 12 carbon atoms.

(3) Amides within the scope of carbonylamino of the formula —$NR_{11}COR_{10}$ are methylcarbonylamide, ethylcarbonylamide, phenylcarbonylamide, and benzylcarbonylamide.

(4) Amides within the scope of sulfonylamino of the formula —NR$_{11}$SO$_2$R$_{10}$ are methylsulfonylamide, ethylsulfonylamide, phenylsulfonylamide, p-tolylsulfonylamide, benzylsulfonylamide.

Examples of alkyl of one to 12 carbon atoms, inclusive, are methyl, ethyl, propyl, isopropyl, isobutyl, tert-butyl, isopentyl, neopentyl, butyl, pentyl, hexyl, heptyl, octyl, nonyl, decyl, undecyl, dodecyl, isomeric forms thereof.

Examples of (C$_3$–C$_{10}$)cycloalkyl which includes alkyl-substituted cycloalkyl, are cyclopropyl, 2-methylcyclopropyl, 2,2-dimethylcyclopropyl, 2,3,-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of (C$_7$–C$_{12}$)aralkyl are benzyl, 2-phenylethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclsive, are p-chlorophenyl, m-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2methylphenyl, and 2,4-dichloro-3-methylphenyl.

The terms phthalidyl; 3-(5,5-dimethyl-1,3,2-dioxaphosphorinan-2-yl)-2-oxopropan-1-yl P-oxide; and 3-(5,5-di(hydroxymethyl)-1,3,2-dioxaphosphorinan-2-yl)-2-oxopropan-1-yl P-oxide; which R$_5$ may represent in the —COOR$_5$ group mean the following respective moieties (a), (b) and (c):

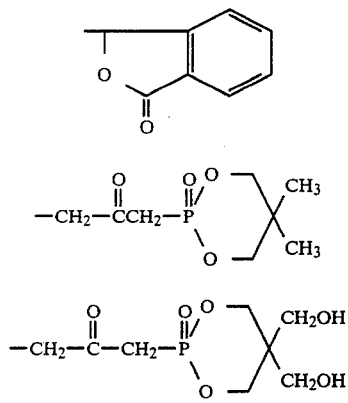

It will be noted hereinbelow that during the preparation of the compounds of Formula IV it is desirable that the C-11 hydroxy groups which may be present be protected. Also, during the conversion of the C-1 position carboxyl groups to the various other C-1 position groups represented by Q it is preferred that the C-15 position hydroxyl groups be protected. Suitable protecting groups are herein defined as the group R$_{12}$ which is any group which replaces a hydroxy hydrogen and is neither attacked by nor is reactive to the reagents used in the transformations described herein as a hydroxy is and which is subsequently hydrolyzed to give the free hydroxyl group. Several such protective groups are known in the art, e.g., tetrahydropyranyl and substituted tetrahydropyranyl. See for reference E. J. Corey, Proceedings of the Robert A. Welch Foundation Conferences on Chemical Research, XII Organic Synthesis, pp. 51-79 (1969). Those blocking groups which have been found useful include:

(a) tetrahydropyranyl;
(b) tetrahydrofuranyl;
(c) a group of the formula —C(OR$_3$)(R$_{18}$)—CH(R$_{19}$)(R$_4$), wherein R$_3$ is alkyl of one to 18 carbon atoms, inclusive, cycloalkyl of 3 to 10 carbon atoms, inclusive, aralkyl of 7 to 12 carbon atoms, inclusive, phenyl or phenyl substituted with one to 3 alkyl of one to 4 carbon atoms, inclusive, wherein R$_{18}$ and R$_{19}$ are alkyl of one to 4 carbon atoms, inclusive, phenyl, phenyl substituted with one, 2 or 3 alkyl of one to 4 carbon atoms, inclusive, or when R$_{18}$ and R$_{19}$ are taken together —(CH$_2$)$_a$— or when R$_{18}$ and R$_{19}$ are taken together to form —(CH$_2$)$_b$—O—(CH$_2$)$_c$, wherein a is 3, 4, or 5 and b is one, 2, or 3, and c is one, 2, or 3, with the proviso that b plus c is 2, 3, or 4, with the further proviso that R$_{18}$ and R$_{19}$ may be the same or different, and wherein R$_4$ is hydrogen or phenyl; and
(d) silyl groups according to R$_2$, as qualified hereinafter.

When the protective group R$_{12}$ is tetrahydropyranyl, the tetrahydropyranyl ether derivative of any hydroxy moieties of the CBA-type intermediates herein is obtained by reaction of the hydroxy-containing compound with 2,3-dihydropyran in an inert solvent, e.g., dichloromethane, in the presence of an acid condensing agent such as p-toluenesulfonic acid or pyridine hydrochloride. The dihydropyran is used in large stoichiometric excess, preferably 4 to 100 times the stoichiometric amount. The reaction is normally complete in less than an hour at 20°–50° C.

When the R$_{12}$ protective group is tetrahydrofuranyl, 2,3-dihydrofuran is used, as described in the preceding paragraph, in place of the 2,3-dihydropyran.

When the R$_{12}$ protective group is of the formula —C(OR$_3$)(R$_{18}$)—CH(R$_{19}$)(R$_4$), wherein R$_3$, R$_{18}$, R$_{19}$, and R$_4$ are as defined above; a vinyl ether or an unsaturated cyclic or heterocyclic compound, e.g., 1-cyclohexen-1-yl methyl ether, or 5,6-dihydro-4-methoxy-2H-pyran is employed. See C. B. Reese, et al., J. American Chemical Society 89, 3366 (1967). The reaction conditions for such vinyl ethers and unsaturated compounds are similar to those for dihydropyran above.

R$_2$ is a silyl protective group of the formula —Si(G$_1$)$_3$. In some cases, such silylations are general, in that they silylate all hydroxyls of a molecule, while in other cases they are selective, in that while one or more hydroxyls are silylated, at least one other hydroxyl remains unaffected. For any of these silylations, silyl groups within the scope of —Si(G$_1$)$_3$ include trimethylsilyl, dimethylphenylsilyl, triphenylsilyl, t-butyldimethylsilyl, or methylphenylbenzylsilyl. With regard to G$_1$, examples of alkyl are methyl, ethyl, propyl, isobutyl, butyl, sec-butyl, tert-butyl, pentyl, and the like. Examples of aralkyl are benzyl, phenethyl, α-phenylethyl, 3-phenylpropyl, α-naphthylmethyl, and 2-(α-naphthyl)ethyl. Examples of phenyl substituted with halo or alkyl are p-chlorophenyl, m-fluorophenyl, o-tolyl, 2,4-dichlorophenyl, p-tert-butylphenyl, 4-chloro-2-methylphenyl, and 2,4-dichloro-3-methylphenyl.

These silyl groups are known in the art. See for example, Pierce "Silylation of Organic Compounds," Pierce Chemical Company, Rockford, Ill. (1968). When silylated products of the charts below are intended to be subjected to chromatographic purification, then the use of silyl groups known to be unstable to chromatography (e.g. trimethylsilyl) is to be avoided. Further, when silyl groups are to be introduced selectively, silylating agents which are readily available and known to be useful in selective silylations are employed. For example, t-butyldimethylsilyl groups are employed when selective introduction is required. Further, when silyl groups are to be selectively hydrolyzed in the presence of protective groups according to $R_{12}$ or acyl protective groups, then the use of silyl groups which are readily available and known to be easily hydrolyzable with tetra-n-butylammonium fluoride are employed. A particularly useful silyl group for this purpose is t-butyldimethylsilyl, while other silyl groups (e.g. trimethylsilyl) are not employed when selective introduction and/or hydrolysis is required.

The protective groups as defined by $R_{12}$ are otherwise removed by mild acidic hydrolysis. For example, by reaction with (1) hydrochloric acid in methanol; (2) a mixture of acetic acid, water, and tetrahydrofuran, or (3) aqueous citric acid or aqueous phosphoric acid in tetrahydrofuran, at temperatures below 55° C., hydrolysis of the blocking group is achieved.

The compounds of formula IV produce certain prostacyclin-like pharmacological responses. Accordingly, the novel formula IV compounds are useful as agents in the study, prevention, control, and treatment of diseases, and other undesirable physiological conditions, in mammals, particularly humans, valuable domestic animals, pets, zoological specimens, and laboratory animals (e.g., mice, rats, rabbits and monkeys). In particular, these compounds are useful as anti-ulcer agents and anti-asthma agents, and as antithrombotic agents as indicated below. The compounds of Formula IV are particularly useful in that said compounds possess an improved ratio of platelet aggregation to blood pressure lowering effects as compared to closely related compounds.

(a) Platelet Aggregation Inhibition

The compounds of formula IV are useful whenever it is desired to inhibit platelet aggregation, to reduce the adhesive character of platelets, or to remove or prevent the formation of thrombi in mammals, including man. For example, these compounds are useful in the treatment and prevention of myocardial infarcts, to treat and prevent post-operative thrombosis, to promote patency of vascular grafts following surgery, to treat peripheral vascular diseases, and to treat conditions such as atherosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., intravenously, subcutaneously, intramuscularly, and in the form of sterile implants for prolonged action. For rapid response, especially in emergency situations, the intravenous route of administration is preferred.

The preferred dosage route for these compounds is oral, although other non-parenteral routes (e.g., buccal, rectal, sublingual) are likewise employed in preference to parenteral routes. Oral dosage forms are conventionally formulated as, e.g., tablets or capsules and administered 2–4 times daily. Doses in the range of about 0.05 to 100 mg per kg of body weight per day are effective in treating the aforedescribed conditions associated with the inhibition of platelet aggregation. Doses in the range about 0.01 to about 10 mg per kg of body weight per day are preferred, the exact dose depending on the age, weight, and condition of the patient or animal, and on the frequency and route of administration.

The addition of these compounds to whole blood provides in vitro applications such as storage of whole blood to be used in heart-lung machines. Additionally whole blood containing these compounds can be circulated through organs, e.g., heart and kidneys, which have been removed from a donor prior to transplant. They are also useful in preparing platelet rich concentrates for use in treating thrombocytopenia, chemotherapy, and radiation therapy. In vitro applications utilize a dose of 0.001–1.0 µg per ml of whole blood. The compounds of the present invention are useful in the treatment of peripheral vascular diseases, in the same manner as described in U.S. Pat. No. 4,103,026.

(b) Gastric Secretion Reduction

Compounds of Formula IV are useful in mammals, including man and certain useful animals, e.g., dogs and pigs, to reduce and control gastric secretion, thereby to reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range of about 0.1 µg to about 20 µg per kg of body weight per minute, or in a total daily dose by injection or infusion in the range about 0.01 to about 10 mg per kg of body weight per day, the exact dose depending on the age, weight, and condition of the patient or animal, and on the frequency and route of administration.

Preferably, however, these novel compounds are administered orally or by other non-parenteral routes. As employed orally, one to 6 administrations daily in a dosage range of about 1.0 to 100 mg per kg of body weight per day is employed. Once healing of the ulcers has been accomplished the maintenance dosage required to prevent recurrence is adjusted downward so long as the patient or animals remains asymptomatic.

(c) NOSAC-Induced Lesion Inhibition

Compounds of Formula IV are also useful in reducing the undesirable gastrointestinal effects resulting from systemic administration of anti-inflammatory prostaglandin synthetase inhibitors, and are useful for that purpose by concomitant administration of said compounds of Formula IV and the anti-inflammatory prostaglandin synthetase inhibitor. See Partridge, et al., U.S. Pat. No. 3,781,429, for a disclosure that the ulcerogenic effect induced by certain non-steroidal anti-inflammatory agents in rats is inhibited by concomitant oral administration of certain prostaglandins of the E series. Accordingly these novel Formula IV compounds are useful, for example, in reducing the undesirable gastrointestinal effects resulting from systemic administration of known prostaglandin synthetase inhibitors, e.g., indomethacin, phenylbutazone, and aspirin, in the same manner as described by Partridge, et al, for the PGE compounds in U.S. Pat. No. 3,781,429.

The anti-inflammatory synthetase inhibitor, for example, indomethacin, aspirin, or phenylbutazone is administered in any of the ways known in the art to alleviate an inflammatory conditions, for example, in any dosage regimen and by any of the known routes of systemic administration.

(d) Bronchodilation (Anti-asthma)

The compounds of Formula IV are also useful in the treatment of asthma. For example, these compounds are useful as bronchodilators or as inhibitors of mediator-induced bronchoconstriction, such as SRS-A, and histamine which are released from cells activated by an antigen-antibody complex. Thus, these compounds control spasm and facilitate breathing in conditions such as bronchial bronchitis, bronchiectasis, pneumonia and emphysema. For these purposes, these compounds are administered in a variety of dosage forms, e.g., orally in the form of tablets, capsules, or liquids; rectally in the form of suppositories, parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg per kg of body weight are used 1 to 4 times a day, the exact dose depending on the age, weight, and condition of the patient and on the frequency and route of administration. For the above use Formula IV compounds can be combined advantageously with other anti-asthmatic agents, such as sympathomimetics (isoproterenol, phenylephrine, ephedrine, etc.); xanthine derivatives (theophylline and aminophylline); and corticosteroids (ACTH and prednisolone).

The pharmacologically useful Formula IV compounds are effectively administered to human asthma patients by oral inhalation or by aerosol inhalation. For administration by the oral inhalation route with conventional nebulizers or by oxygen aerosolization it is convenient to provide the instant active ingredient in dilute solution, preferably at concentrations of about one part of medicament to from about 100 to 200 parts by weight of total solution. Entirely conventional additives may be employed to stabilize these solutions or to provide isotonic media, for example, sodium chloride, sodium citrate, citric acid, sodium bisulfite, and the like can be employed. For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a cosolvent, such as ethanol, flavoring materials and stabilizers. Suitable means to employ the aerosol inhalation therapy technique are described fully in U.S. Pat. No. 3,868,691, for example.

When Q is —COOR$_5$, the novel Formula IV compounds so described are used for the purposes described above in the free acid form, in ester form, or in pharmacologically acceptable salt form. When the ester form is used, the ester is any of those within the above definition of R$_5$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity.

Pharmacologically acceptable salts of the novel compounds of Formula IV for the purposes described above are those with pharmacologically acceptable metal cations, ammonia, amine cations, or quaternary ammonium cations. Illustrative pharmacological acceptable cations which R$_5$ may represent are the following.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, and tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, adamantylamine, and the like aliphatic, cycloaliphatic, aralphatic amines containing up to and including about 18 carbon atoms, as well as heterocyclic amines, e.g., piperidine, morpholine, pyrrolidine, piperazine, and lower-alkyl derivatives thereto, e.g., 1-methylpiperidine, 4-ethylmorpholine, 1-isopropylpyrrolidine, 2-methylpyrrolidine, 1,4-dimethylpiperazine, 2-methylpiperidine, and the like as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl) aminomethane, N-phenylethanolamine, N-(p-tert-amylphenyl)-diethanolamine, galactamine, N-methylglycamine, N-methylglucosamine, ephedrine, phenylephrine, epinephrine, procaine, and the like. Further useful amine salts of the basic amino acid salts, e.g., lysine and arginine.

Examples of suitable pharmacologically acceptable quaternary ammonium cations are tetramethylammonium, tetraethylammonium, benzyltrimethylammonium, phenyltriethylammonium, and the like.

When Q is —CH$_2$NL$_3$L$_4$, the Formula IV compounds so described are used for the purposes described in either free base or pharmacologically acceptable acid addition salt form.

The acid addition salts of the 2-decarboxy-2-aminomethyl- or 2-(substituted aminomethyl)-Formula IV compounds provided by this invention are, for example, the hydrochlorides, hydrobromides, hydriodides, sulfates, phosphates, cyclohexanesulfamates, methane sulfonates, ethanesulfonates, benzenesulfonates, toluenesulfonates and the like, prepared by reacting the appropriate compound of Formula IV with the stoichiometric amount of the acid corresponding to the pharmacologically acceptable acid addition salt.

To obtain the optimum combination of biological response specificity, potency, and duration of activity, certain compounds within the scope of this invention are preferred. Preferred compounds of the present invention are formula IV compounds wherein Z$_4$ is —CH$_2$—, and of these compounds those wherein Y is —CH$_2$CH$_2$—, —C≡C— or trans—CH=CH— and/or Q is —COOR$_5$ or —COL$_2$ are preferred especially when R$_5$ is hydrogen, methyl, ethyl, or a pharmacologically acceptable cation such as sodium, and when each of R$_9$ and R$_{10}$ of the L$_2$ substituent moiety is hydrogen.

To further characterize the preferred embodiments of the present invention, compounds of Formula IV wherein

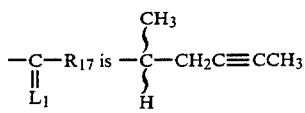

are more preferred and more particularly preferred are the 15(S) compounds. Compounds of Formula IV are prepared by various procedures which are all generally known in the art. The compounds of Formula IV wherein Q is —COOR$_5$ and R$_5$ is hydrogen are prepared by reacting a compound of the formula

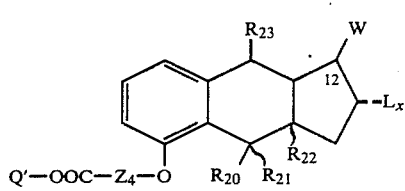

Formula A wherein W is —CHO; Lx is H,H; $\alpha$-OR$_{12}$,$\beta$-H; $\alpha$-H,$\beta$-OR$_{12}$; $\alpha$-CH$_2$OR$_{12}$,$\beta$H; $\alpha$-H,$\beta$-CH$_2$OR$_{12}$ wherein R$_{12}$ is a protecting group as defined hereinabove; Q' is a lower alkyl group such as methyl, ethyl, propyl or butyl; and Z$_4$, R$_{20}$, R$_{21}$, R$_{22}$ and R$_{23}$ have the meanings defined in Formula IV; with the anion of an alkyl phosphonate of the formula

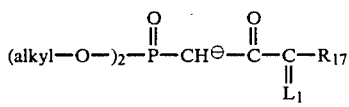

Formula B wherein alkyl is a lower alkyl such as methyl, ethyl, propul or butyl and R$_{17}$ and L$_1$ have the meanings defined in Formula IV, under the conditions of a Wittig reaction to give a ketone intermediate corresponding to Formula A wherein W is the group

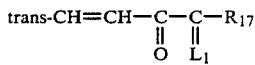

Formula A-1 which is then reduced by hydride reduction to the $\alpha$- or $\beta$-alcohol as defined by M in Formula IV to give compounds of Formula A wherein W is the group

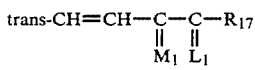

Formula A-2 wherein M$_1$ is a $\alpha$-OH,$\beta$-H or $\alpha$-H,$\beta$-OH and wherein L$_1$ and R$_{17}$ have the meanings defined in Formula IV. The thus obtained trans-vinyl compounds can be hydrogenated to give corresponding compounds of Formula A wherein W is the group

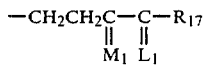

Formula A-3 or can be halogenated followed by tetradehydrohalogenation to give the corresponding compounds of Formula A wherein W is the group

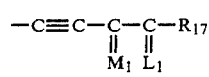

Formula A-4

Hydrogenation of the thus obtained acetylene containing compounds with a Lindlar catalyst give the corresponding cis-vinyl compounds, i.e., Formula A wherein W is the group

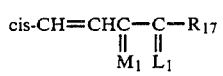

Formula A-5

Once the appropriate transformations at the C-12 position are completed to give the Formula A-2, A-3, A-4 and A-5 compounds, the C-11 protecting group is removed by hydrolysis to give the C-11 free hydroxyl compound, and the C-1 position carboxylic acid ester is hydrolyzed to the free acid by standard procedures known in the art.

The compounds of Formula IV wherein Q is —COOR$_5$ and R$_5$ is hydrogen are also prepared by treating a compound of Formula A with a phosphine of the formula (alkyl)$_3$—P=CHCHO under the conditions of a Wittig reaction to give the corresponding compounds of Formula A wherein W is trans-vinyl aldehyde group of the formula trans—CH=CHCHO which is reduced to the corresponding trans-vinyl alcohol, i.e., Formula A wherein W is trans—CH=CHCH$_2$OH. The trans-vinyl alcohol can be hydrogenated to give Formula A compounds wherein W is the group —CH$_2$CH$_2$CH$_2$OH, or the trans-vinyl alcohol can be halogenated then tetradehydrohalogenated to give the corresponding acetylene alcohol, i.e., compounds of Formula A wherein W is the group —C≡CCH$_2$OH. Hydrogenation of the acetylene alcohol with a Lindlar catalyst gives the corresponding cis-vinyl alcohols, i.e., Formula A compounds wherein W is the group cis-CH=CHCH$_2$OH.

The thus obtained alcohols, i.e., compounds of Formula A wherein W is trans—CH=CHCH$_2$OH, —CH$_2$CH$_2$CH$_2$OH, —C≡CCH$_2$OH or cis—CH=CHCH$_2$OH are oxidized to the corresponding aldehydes then treated with a Grignard reagent of the formula halo MgCpH$_2$pCH=CH$_2$, wherein halo is a halogen or an alkyl lithium of the formula LiCpH$_2$pCH=CH$_2$, or an acetylide anion of the formula —C≡CCpH$_2$pCH$_3$ or an anion of the formula

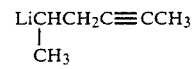

to give compounds of Formula A wherein W is

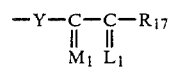

Formula A-6 wherein Y, L$_1$ and R$_{17}$ have the meanings defined in Formula IV and M$_1$ is $\alpha$-OH,$\beta$-H or $\alpha$-H,$\beta$-OH. The C-11 protecting group of the Formula A-6 compounds is then hydrolyzed to give the C-11 position free hydroxyl, and the C-1 position carboxylic acid ester is hydrolyzed to the corresponding free acid by standard procedures.

To prepare compounds of Formula IV wherein $R_{14}$ of the M substituent group is —$CH_3$ the C-15 alcohols of Formulas A-2, A-3, A-4, A-5 and A-6 are oxidized to the corresponding C-15 ketone then treated with methyl lithium or a methyl Grignard by procedures known in the art followed by hydrolysis of the C-11 protecting group of the C-1 ester to free acid.

It is understood that in the foregoing description the compounds of Formulas A-1 to A-6 are those of Formula A wherein W has the meaning defined in connection with each of Formulas A-1 to A-6.

The compounds of Formula A wherein W is —CHO are described in U.S. Pat. No. 4,306,075 the pertinent portions of which and in particular the information comprising Chart S at columns 93 and 94 and Chart U at column 95 and column 27, line 57 to column 28, line 25 and specific Examples 31 and 36 wherein the synthesis of said compounds is described, is incorporated herein by reference thereto.

The compounds of Formula B are prepared by addition of the anion of a dialkyl methyl phosphonate of the formula

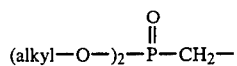

wherein alkyl is, e.g., methyl, ethyl, propyl or butyl with an ester of the formula

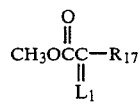

wherein $L_1$ and $R_{17}$ have the meanings defined in Formula IV by procedures well known in the art, followed by treatment with base (e.g., sodium hydride).

In preparing compounds of Formula IV wherein Q is other than COOH, the C-1 carboxylic acids are esterified or converted to an amide derivative by conventional means. Also, the acid or an ester thereof can be reduced to the corresponding alcohol, i.e., Formula IV wherein Q is —$CH_2OH$ by standard procedures, e.g., by refluxing with lithium aluminum hydride in an ether solvent. The alcohol thus obtained or a carboxylic acid ester derivative of Formula IV can be oxidized to the corresponding carboxaldehyde which upon treatment with a salt of hydroxylamine gives the oxime which is dehydrated to give the nitrile, i.e., the compounds of Formula IV wherein Q is CN. These conversions are all carried out by procedures generally known in the art. See, for example, the aforementioned British specifications which describe the synthesis of various carbacyclin compounds, and in particular G.B. 2,013,661. The amide thus obtained can be reduced to the corresponding amines, i.e., compounds of Formula IV wherein Q is —$CH_2NL_3L_4$ by using, e.g., lithium aluminum hydride. See U.S. Pat. No. 4,073,808. Of course during the conversion of the Formula IV acids to the various other C-1 position derivatives of the present invention, the C-11 and C-15 hydroxyl groups are protected with an $R_{12}$ protecting group as described herein which groups are ultimately removed by hydrolysis.

When a C-1 position alkyl ester is obtained and the acid is desired saponification procedures known in the art are employed.

When an acid of the present invention has been prepared and an alkyl, cycloalkyl, or aralkyl ester is desired, esterification is advantageously accomplished by interaction of the acid with appropriate diazohydrocarbon. For example, when diazomethane is used, the methyl ester is produced. Similar use of diazoethane, diazobutane, and 1-diazo-2-ethylhexane, and diazodecane, for example, gives the ethyl, butyl, and 2-ethylhexyl and decyl esters, respectively. Similarly, diazocyclohexane and phenyldiazomethane yield cyclohexyl and benzyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete the solvent is removed by evaporation, and the ester purified if desired by conventional methods, preferably by chromatography. It is preferred that contact of the acid reactants with the diazohydrocarbon be no longer than necessary to effect the desired esterification, preferably about one to about 10 minutes, to avoid undesired molecular changes. Diazohydrocarbons are known in the art or can be prepared by methods known in the art. See, for example, Organic Reactions, John Wiley and Sons, Inc., New York, N.Y., Vol. 8, pp. 389–394 (1954).

An alternative method for alkyl, cycloalkyl or aralkyl esterification of the carboxy moiety of the acid compounds comprises transformation of the free acid to the coresponding substituted ammonium salt, followed by interaction of that salt with an alkyl iodide. Examples of suitable iodides are methyl iodide, ethyl iodide, butyl iodide, isobutyl iodide, tert-butyl iodide, cyclopropyl iodide, cyclopentyl iodide, benzyl iodide, phenethyl iodide, and the like.

Various methods are available for preparing phenyl or substituted phenyl esters within the scope of the invention from corresponding aromatic alcohols and the free acid, differing as to yield and purity of product.

With regard to the preparation of the phenyl, particularly p-substituted phenyl esters disclosed herein (i.e., Q is $COOR_5$ and $R_5$ is p-substituted phenyl), such compounds are prepared by the method described in U.S. Pat. No. 3,890,372. Accordingly, by the preferred method described therein, the p-substituted phenyl ester is prepared first by forming a mixed anhydride, particularly following the procedures described below for preparing such anhydrides as the first step in the preparation of amido and cycloamido derivatives.

This anhydride is then reacted with a solution of the phenol corresponding to the p-substituted phenyl ester to be prepared. This reaction proceeds preferably in the presence of a tertiary amine, such as pyridine. When the conversion is complete, the p-substituted phenyl ester has been recovered by conventional techniques.

A preferred method for substituted phenyl esters is that disclosed in U.S. Pat. No. 3,890,372 in which a mixed anhydride is reacted with an appropriate phenol or naphthol. The anhydride is formed with an appropriate phenol or naphthol. The anhydride is formed from the acid with isobutylchloroformate in the presence of a tertiary amine.

Phenacyl-type esters are prepared from the acid using a phenacyl bromide, for example p-phenylphenacyl bromide, in the presence of a tertiary amine. See, for example, U.S. Pat. No. 3,984,454, German Offenlegungsschrift 2,535,693, and Derwent Farmdoc No. 16828X.

The phthalidyl esters are obtained by treating the corresponding acid with a phthalidyl halide such as the bromide in, e.g., dimethylformamide in the presence of an amine base. The phosphoranyl esters are obtained by treating the corresponding acid with a 1-halo derivative, e.g., the 1-chloro derivative of 3-(5,5-di(hydroxymethyl)-1,3,2-dioxaphosphorinan-2-yl)-2-oxopropan-1-yl P-oxide and 3-(5,5-dimethyl-1,3,2-dioxaphosphorinan-2-yl)-2-oxopropan-1-yl P-oxide in, e.g., acetonitrile in the presence of an organic amine.

Carboxyamides (Q is $-COL_2$) are prepared by one of several amidation methods known in the prior art. See, for example, U.S. Pat. No. 3,981,868, issued 21 Sept. 1976 for a description of the preparation of the present amido and cycloamido derivatives of prostaglandin-type free acids and U.S. Pat. No. 3,954,741 describing the preparation of carbonylamido and sulfonylamido derivatives of prostagladin-type free acids.

The preferred method by which the present amido and cycloamido derivatives of the acids are prepared is, first, by transformation of such free acids to corresponding mixed acid anhydrides. By this procedure, the free acid is first neutralized with an equivalent of an amine base, and thereafter reacted with a slight stoichiometric excess of a chloroformate corresponding to the mixed anhydride to be prepared.

The amine base preferred for neutralization is triethylamine, although other amines (e.g., pyridine, methyldiethylamine) are likewise employed. Further, a convenient, readily available chloroformate for use in the mixed anhydride production is isobutyl chloroformate.

The mixed anhydride formation proceeds by conventional methods and accordingly the free acid is mixed with both the tertiary amine base and the chloroformate in a suitable solvent (e.g., aqueous tetrahydrofuran), allowing the reaction to proceed at $-10°$ C. to 20° C.

Thereafter, the mixed anhydride is converted to the corresponding amido or cycloamido derivatives by reaction with the amine corresponding to the amide to be prepared. In the case where the simple amide ($-NH_2$) is to be prepared, the transformation proceeds by the addition of ammonia. Accordingly, the corresponding amine (or ammonia) is mixed with the mixed anhydride at or about $-10°$ to $+10°$ C., until the reaction is shown to be complete.

Thereafter, the novel amido or cycloamido derivative is recovered from the reaction mixture by conventional techniques.

The carbonylamido and sulfonylamido derivative of the present invention are likewise prepared by known methods. See, for example, U.S. Pat. No. 3,954,741 for description of the methods by which such derivatives are prepared. By this known method the acid is reacted with a carboxyacyl or sulfonyl isocyanate, corresponding to the carbonylamido or sulfonylamido derivative to be prepared.

By another, more preferred method the sulfonylamido derivatives of the present compounds are prepared by first generating the mixed anhydride, employing the method described above for the preparation of the amido and cycloamido derivatives. Thereafter, the sodium salt of the corresponding sulfonamide is reacted with the mixed anhydride and hexamethylphosphoramide. The pure sulfonylamido derivative is then obtained from the resulting reaction mixture by conventional techniques.

The sodium salt of the sulfonamide corresponding to the sulfonylamido derivative to be prepared is generated by reacting the sulfonamide with alcoholic sodium methoxide. Thus, by a preferred method methanolic sodium methoxide is reacted with an equal molar amount of the sulfonamide. The sulfonamide salt is then reacted, as described above, with the mixed anhydride, using about four equivalents of the sodium salt per equivalent of anhydride. Reaction temperatures at or about 0° C. are employed.

The compounds of this invention prepared by the processes of this invention, in free acid form, are transformed to pharmacologically acceptable salts by neutralization with appropriate amounts of the corresponding inorganic or organic base, examples of which correspond to the cations and amines listed hereinabove. These transformations are carried out by a variety of procedures known in the art to be generally useful for the preparation of inorganic, i.e., metal or ammonium salts. The choice of procedure depends in part upon the solubility characteristics of the particular salt to be prepared. In the case of the inorganic salts, it is usually suitable to dissolve an acid of this invention in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, an acid of this invention is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by evaporation. If the amine is relatively volatile, any excess can easily be removed by evaporation. It is preferred to use stoichiometric amounts of the less volatile amines.

Salts wherein the cation is quaternary ammonium are produced by mixing an acid of this invention with the stoichiometric amount of the corresponding quaternary ammonium hydroxide in water solution, followed by evaporation of the water.

EXAMPLE 1

(a)

9,15-Dideoxy-15-keto-2′,9α-methano-16-methyl-3-oxa-18,19-tetradehydro-4,5,6-trinor-3,7-(1′,3′-interphenylene)-PGF$_1$, methyl ester, 11-tetrahydropyranyl ether A suspension of 18 mg (0.43 mmol) of sodium hydride (57% dispersion in mineral oil) in 1.5 ml of dry THF at 0° under argon was treated with 100 mg (0.43 mmol) of dimethyl-2-oxo-3-methyl-5-heptynylphosphonate using 2 ml of dry tetrahydrofuran (THF) for the transfer. The resulting solution was stirred for five minutes at 0° and one hour at room temperature, cooled to 0° and treated with a solution of 0.14 g (0.36 mmol) of aldehyde 9-deoxy-2′,9α-methano-3-oxa-4,5,6,13,14,15,16,17,18,19,20-undecanor-3,7-(1′,3′-interphenylene)-12-formyl-PGF$_1$, methyl ester in 2.5 ml of dry THF. The resulting solution was stirred for 2.5 hours at room temperature, cooled to 0°, diluted with 40 ml of water containing two drops of acetic acid, and extracted with three 40 ml portions of ethyl acetate. The combined ethyl acetate extracts were washed with 30 ml of bicarb and 30 ml of brine and were dried over anhydrous sodium sulfate. The solvents were removed under reduced pressure and the residue chromatographed on silica gel eluting with 2:1 hexane-ethyl acetate to give 167 mg (94%) of the title compound as a colorless oil.

NMR (CDCl$_3$; TMS): δ 0.90–3.1 (m including 3H doublet, J=7 Hz at 1.18 δ and 3H triplet, J=3 Hz, at 1.75 δ, 24H), 3.10–4.2 (m including 3H singlet at 3.86 δ, 6H), 4.60 (s, 3H), 6.06–7.28 (m, 5H).

Infrared: νmax (film): 1765, 1720, 1620, 1590, 1470, 1240, 1200, 1120, 1025, 975 cm$^{-1}$.

TLC: (Silica Gel GF); R$_f$ 0.32 in 2:1 hexane-ethyl acetate (UV active).

(b)

9-Deoxy-2',9α-methano-16-methyl-3-oxa-18,19-tetradehydro-4,5,6-trinor-3,7-(1',3'-interphenylene)-15-epi-PGF$_1$, methyl ester (6), and 9-Deoxy-2',9α-methano-16-methyl-3-oxa-18,19-tetradehydro-4,5,6-trinor-3,7-(1',3'-interphenylene)-PGF$_1$, methyl ester (7)

A solution of 18 mg (0.48 mmol) of sodium borohydride in 2 ml of methanol at −30° under nitrogen was treated dropwise with a solution of 166 mg (0.336 mmol) of ketone from 1(a) above and 0.15 ml of methylene chloride in 1.5 ml of methanol. The resulting solution was stirred at −30° for 1.5 hours, at −20° for one hour, and then at −10° to −15° for one hour, quenched at −20° with 0.1 ml of glacial acetic acid, added to 40 ml of brine, and extracted with three 40 ml portions of ethyl acetate. The combined ethyl acetate extracts were washed with 40 ml of bicarb and 40 ml of brine and were dried over anhydrous sodium sulfate. The solvents were removed under reduced pressure and the residue chromatographed on silica gel eluting with 40% ethyl acetate in hexane to give 161 mg (97%) of an alcohol mixture used without further purification.

A solution of the above obtained 161 ml (0.324 mmol) of alcohol in 1.5 ml of THF, 2.3 ml of water, and 4.5 ml of glacial acetic acid was heated at 40°–45° for three hours, cooled, diluted with 50 ml of brine, and extracted with two 50 ml portions of ethyl acetate. The combined ethyl acetate extracts were washed with 50 ml of brine, with three 50 ml portions of bicarb, and 50 ml of brine, and were dried over anhydrous sodium sulfate. The solvents were removed under reduced pressure and the residue chromatographed on 25 g of silica gel eluting with 125 ml of 20% acetone in methylene chloride, then 100 ml of 40% acetone in methylene chloride, then 50% acetone in methylene chloride to give 45 mg (34%) of alcohol 6 and 84 mg (63%) of alcohol 7, both colorless oils.

For compound 6:

NMR (CDCl$_3$; TMS): δ 0.7–3.0 (m including 3H triplet, J=2 Hz at 1.88 δ, 20H), 3.53–4.3 (m including 3H singlet at 3.76 δ, 5H), 4.62 (s, 2H), 5.51–5.75 (m, 2H), 6.53–7.73 (m, 3H).

Infrared: νmax (film): 3400, 1765, 1740, 1590, 1470, 1440, 1280, 1210, 1120, 1020, 975 cm$^{-1}$.

TLC (Silica Gel GF): R$_f$ 0.31 in 20% acetone in methylene chloride.

For compound 7:

NMR (CDCl$_3$; TMS): δ 0.8–3.4 (m including 3H triplet, J=2 Hz at 1.78 δ, 20H), 3.48–4.35 (m including 3H singlet at 3.76 δ, 5H), 4.60 (s, 2H), 5.37–5.70 (m, 2H), 6.53–7.30 (m, 3H).

Infrared: νmax (film): 3390, 1760, 1740, 1590, 1470, 1440, 1375, 1210, 1120, 1020, 970 cm$^{-1}$.

TLC (Silica Gel GF): R$_f$ 0.16 in 20% acetone in methylene chloride.

(c)

9-Deoxy-2',9α-methano-16-methyl-3-oxa-18,19-tetradehydro-4,5,6-trinor-3,7-(1',3'-interphenylene)-PGF$_1$ A solution of 75 mg (0.18 mmol) of ester 7 from 1(b) above and 2 ml of 10% potassium hydroxide (in 9:1 methanol-water) in 2 ml of 9:1 methanol-water stirring at 0° under argon was allowed to slowly warm to room temperature. After 17 hours the resulting solution was added to 50 ml of cold brine, acidified with 1N aqueous hydrochloric acid, and extracted with three 50 ml portions of ethyl acetate. The combined ethyl acetate extracts were washed with 50 ml of brine and dried over anhydrous sodium sulfate. The solvents were removed in vacuo and the residue crystallized form hot hexane and ether to give 60 mg (83%) of the title compound a a white solid, m.p. 132°–136°.

NMR (CDCl$_3$; TMS): δ 0.70–2.90 (m including 3H triplet, J=2 Hz at 1.73 δ, 18H), 3.0–4.5 (m, 5H), 4.66 (s, 2H), 5.4–5.68 (m, 2H), 6.6–7.3 (m, 3H).

Infrared: νmax (film): 3290, 1735, 1720, 1470, 1465, 1440, 1380, 1290, 1250, 1125, 1115, 975 cm$^{-1}$.

TLC (Silica Gel GF): R$_f$ 0.20 in the organic phase of 9:2:5:10 EtOAc-HOAc-cyclohexane-water.

(d)

9-Deoxy-2',9α-methano-16-methyl-3-oxa-18,19-tetradehydro-4,5,6-trinor-3,7-(1',3'-interphenylene)-15-epi-PGF$_1$ A solution of 44 mg (0.11 mmol) of ester 6 from 1(b) above and 2 ml of 10% potassium hydroxide (in 9:1 methanol-water) in 2 ml of 9:1 methanol-water stirring at 0° under argon was allowed to slowly warm to room temperature, and after 18 hours added to 50 ml of cold brine, acidified with 1N aqueous HCl, and extracted with three 50 ml portions of ethyl acetate. The combined ethyl acetate extracts were washed with 50 ml of brine and dried over anhydrous sodium sulfate. The solvents were removed in vacuo and the residue crystallized from hot hexane and ether to give 38 mg (89%) of the title compound as a white solid, m.p. 74°–76°.

NMR (CDCl$_3$; TMS): δ 0.70–3.0 (m including 3H triplet, J=2 Hz at 1.78 δ, 18H), 3.4–4.3 (m including 3H singlet at 4.11 δ 5H), 4.66 (s, 2H), 5.4–5.65 (m, 2H), 6.5–7.3 (m, 3H).

Infrared: νmax (film): 3415, 1740, 1710, 1585, 1465, 1460, 1425, 1380, 1370, 1260, 1120, 1090, 970 cm$^{-1}$.

TLC (Silica Gel GF): R$_f$0.27 in the organic phase of 9:2:5:10 EtOAc-HOAc-cyclohexane-H$_2$O.

EXAMPLE 2

(a) 1-Bromo-2-butyne

To a stirred solution of 2-butyne-1-ol (10.0 g, 0.143 mol) in 30 ml of ether at 0° C. is added pyridine (4.84 g, 0.06 mol, 0.43 eq) at once followed by careful dropwise addition of phosphorous tribromide (26.3 g, 0.097 mol, 0.68 eq) over a 30 minute period. An additional 10 ml of ether was added to facilitate stirring and the contents warmed to reflux for 2 hours. The reaction mixture is cooled in ice bath, treated cautiously with 70 ml of ice water and extracted with ether (2×150 ml). The combined ether extracts are washed with saturated brine (2×25 ml), the combined aqueous washings extracted with ether (1×50 ml) and the combined organic extracts dried over anhydrous sodium sulfate. The filtrate is concentrated on a rotary evaporator while keeping the water bath temperature less than 10° C. Twice the contents are diluted with 100 ml of pentane and reconcentrated as before. The heterogenous looking oil is dissolved in 300 ml of pentane, dried over anhydrous magnesium sulfate and reconcentrated as before to obtain 11.0 g (58%) of 1-bromo-2-butyne.

(b) 2-Methyl-4-hexynoic acid

Diisopropylamine (26.0 g, 0.257 mmol, 3.1 eq) in 130 ml of tetrahydrofuran initially at −50° C. is treated dropwise with n-butyl-lithium (98.8 ml, 1.6M, 0.158 mol, 1.9 eq) over an 8 minute period while allowing the temperature to rise to −25° C. After 5 minutes longer at −20° C., the reaction mixture is treated dropwise with a mixture of hexamethylphosphoramide (17.8 g, 0.099 mol, 1.2 eq) and propionic acid (6.14 g, 0.083 mol, 1.0 eq) over a 7 minute period while the temperature rises to 0° C. Following addition the reaction mixture is warmed to room temperature and maintained there for 35 minutes. The contents are then cooled to 0° C. in an ice bath, treated dropwise over a 12 minute period with 1-bromo-2-butyne (11.0 g, 0.083 mol, 1.0 eq) in 8 ml of tetrahydrofuran. The temperature, which rises to 16° C. during addition, is allowed to warm to room temperature thereafter where it is maintained for 2 hours. The contents are carefully poured into 300 ml of 10% HCl with stirring (exothermic) followed by 500 ml of ether-pentane (1:1). The organic layer is separated and the aqueous phase extracted 2 more times with ether-pentane (1:1) giving 1800 ml of total extract volume. The combined extracts are washed with water 2×60 ml) and the combined organic extracts are dried over anhydrous sodium sulfate, magnesium sulfate and concentrated at reduced pressure to provide 11.1 g (over theory) of 2-methyl-4-hexynoic acid which is converted to the methyl ester by treatment with methyl iodide.

(c) 3-Methyl-2-oxo-hept-5-yne phosphonic acid dimethyl ester

A solution of dimethyl methylphosphonate (22.47 g, 181.24 mmol) in 260 ml of tetrahydrofuran is cooled to −78° C. and treated dropwise with n-butyllithium (113 ml, 181.24 mmol), 1.6M in hexane) over a 25-minute period. The mixture is stirred an additional 30 minutes at −78° C., then treated dropwise with 2-methyl-4-hexynoic acid methyl ester (7.25 g, 51.78 mmols) in 65 ml of tetrahydrofuran over a period of 10 minutes. The contents are stirred for another 3 hours at −78° C. and then 17 hours at ambient temperature. The reaction mixture is cooled to 8° C., treated with 14 ml of acetic acid, stirred at ambient temperature for 30 minutes, then concentrated in vacuo. The residue is treated with 100 ml of saturated brine and 100 ml of ice water to form a slurry and extracted 3 times with ether (1400 ml total) and once with 250 ml of ethyl acetate-ether (1:1). The combined organic extracts are washed with saturated brine (2×75 ml), the combined aqueous washings extracted with ethyl acetate-ether (1:1, 1×100 ml) and dried over anhydrous sodium sulfate, and concentrated at reduced pressure. Vacuum distillation gives 10.21 g of the title product, m.p. 121°-125° C., 0.15 mmHg.

EXAMPLE 3

When in the procedure of Example 2(c) 2hexynoic acid, or 5-hexenoic acid is substituted for 2-methyl-4-hexynoic acid one obtains 2oxo-hept-3-yne phosphonic acid dimethyl ester, and 2-oxo-hept-6-ene phosphonic acid dimethyl ester.

EXAMPLE 4

When in the procedure of Example 1(a) one substitues each of the phosphonic acid dimethyl ester compounds from Example 3 for dimethyl-2-oxo-3-methyl-hept-5-ynylphosphonate and the procedure of Example 1(a) through (d) is followed the following respective products are obtained: 9-deoxy-2′,9α-methano-3-oxa-16,17-tetradehydro-4,5,6-trinor-3,7(1′,3′-interphenylene)-PGF$_1$ and the corresponding 15-epi compound; and 9-deoxy-2′,9α-methano-3-oxa-19,20-dehydro-4,5,6-trinor-3,7-( 1′,3′-interphenylene)-PGF$_1$ and the corresponding 15-epi compound.

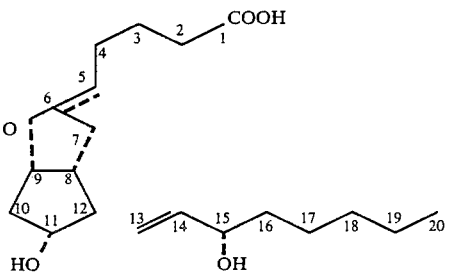

Formula I

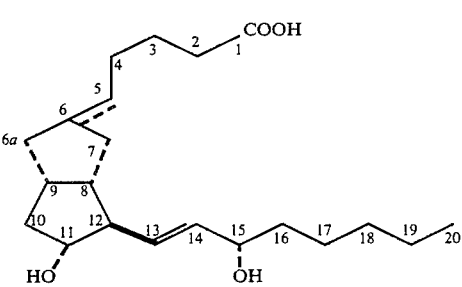

Formula II

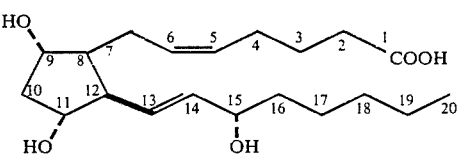

Formula III

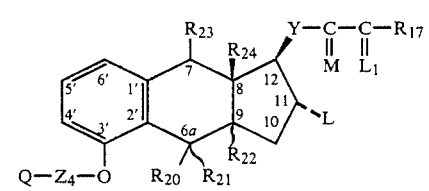

Formula IV

I claim:

1. A compound of the formula

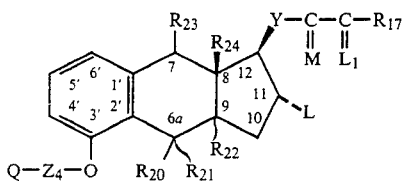

wherein Q is
(1) —COOR$_5$, wherein R$_5$ is
  (a) hydrogen,
  (b) (C$_1$–C$_{12}$)alkyl,
  (c) (C$_3$–C$_{10}$)cycloalkyl,
  (d) (C$_7$–C$_{12}$)aralkyl,
  (e) phenyl optionally substituted with one, 2 or 3 chloro or (C$_1$–C$_4$)alkyl,
  (f) phenyl substituted in the para-position with —NHCOR$_6$, —COR$_7$, —OC(O)R$_8$ or —CH=N—NHCONH$_2$, wherein R$_6$ is methyl, phenyl, acetamidophenyl, benzamidophenyl or —NH$_2$; R$_7$ is methyl, phenyl, —NH$_2$, or methoxy; and R$_8$ is phenyl or acetamidophenyl;
  (g) phthalidyl,
  (h) 3-(5,5-dimethyl-1,3,2-dioxaphosphorinan-2-yl)-2-oxopropan-1-yl P-oxide,
  (i) 3-(5,5-di(hydroxymethyl)-1,3,2-dioxaphosphorinan-2yl)-2-oxopropan-1-yl P-oxide, or
  (j) a pharmacologically acceptable cation;
(2) —CH$_2$OH;
(3) —COL$_2$, wherein L$_2$ is
  (a) an amino group of the formula —NR$_9$R$_{10}$ wherein R$_9$ is hydrogen or (C$_1$–C$_{12}$)alkyl and R$_{10}$ is
    (i) hydrogen
    (ii) (C$_1$–C$_{12}$)alkyl
    (iii) (C$_3$–C$_{10}$)cycloalkyl,
    (iv) (C$_7$–C$_{12}$)aralkyl
    (v) phenyl optionally substituted with one, 2 or 3 chloro, (C$_1$–C$_3$)alkyl, hydroxy, carboxy, (C$_2$–C$_5$)alkoxycarbonyl, or nitro,
    (vi) (C$_2$–C$_5$)carboxyalkyl,
    (vii) (C$_2$–C$_5$)carbamoylalkyl,
    (viii) (C$_2$–C$_5$)cyanoalkyl,
    (ix) (C$_3$–C$_6$)acetylalkyl,
    (x) (C$_7$–C$_{12}$)benzoalkyl, optionaly substituted by one, 2, or 3 chloro, (C$_1$–C$_3$)alkyl, hydroxy, (C$_1$–C$_3$)alkoxy, carboxy, (C$_2$–C$_5$)-alkoxycarbonyl, or nitro,
    (xi) pyridyl, optionally substituted by one, 2, or 3 chloro, (C$_1$–C$_3$)alkyl, or (C$_1$–C$_3$)alkoxy,
    (xii) (C$_6$–C$_9$)pyridylalkyl optionally substituted by one, 2, or 3 chloro, (C$_1$–C$_3$)alkyl, hydroxy, or (C$_1$–C$_3$)alkyl,
    (xiii) (C$_1$–C$_4$)hydroxyalkyl,
    (xiv) (C$_1$–C$_4$)dihydroxyalkyl,
    (xv) (C$_1$–C$_4$)trihydroxyalkyl;
  (b) cycloamino selected from the group consisting of pyrolidino, piperidino, morpholino, piperazino, hexamethyleneimino, pyrroline, or 3,4-didehydropiperidinyl optionally substituted by one or 2(C$_1$–C$_{12}$)alkyl;
  (c) carbonylamino of the formula —NR$_{11}$COR$_{10}$, wherein R$_{11}$ is hydrogen or (C$_1$–C$_4$)alkyl and R$_{10}$ is other than hydrogen, but otherwise defined as above;
  (d) sulfonylamino of the formula —NR$_{11}$SO$_2$R$_{10}$, wherein R$_{11}$ and R$_{10}$ are defined in (c);
(4) —CH$_2$NL$_3$L$_4$, wherein L$_3$ and L$_4$ are hydrogen or (C$_1$–C$_4$)alkyl, being the same or different, or the pharmacologically acceptable acid addition salts thereof when Q is —CH$_2$NL$_3$L$_4$; or
(5) —CN;
wherein Z$_4$ is —CH$_2$— or —(CH$_2$)$_f$—CF$_2$— wherein f is zero, one, 2, or 3;
wherein
(1) R$_{20}$, R$_{21}$, R$_{22}$, R$_{23}$, and R$_{24}$ are all hydrogen with R$_{22}$ being either α-hydrogen or β-hydrogen; or
(2) R$_{20}$ is hydrogen, R$_{21}$ and R$_{22}$ taken together form a second valence bond between C-9 and C-6a, and R$_{23}$ taken together with R$_{24}$ form a second valence bond between C-7 and C-8 or are both hydrogen, or
(3) R$_{22}$, R$_{23}$, and R$_{24}$ are all hydrogen with R$_{22}$ being either α-hydrogen or β-hydrogen, and
  (a) R$_{20}$ and R$_{21}$ taken together are oxo, or
  (b) R$_{20}$ is hydrogen and R$_{21}$ is hydroxy, being α-hydroxy or β-hydroxy;
wherein L is H,H; α-OH,β-H; α-H,β-OH; α-CH$_2$OH,β-H; α-H,β-CH$_2$OH;
wherein Y is trans —CH=CH—, cis—CH=CH—, —CH$_2$CH$_2$—, or —C≡C—; wherein M is α-OH,β-R$_{14}$; or α-R$_{14}$,β-OH, wherein R$_{14}$ is hydrogen or methyl;
wherein L$_1$ is α-R$_{15}$,β-R$_{16}$; α-R$_{16}$,β-R$_{15}$; or a mixture thereof wherein R$_{15}$ and R$_{16}$ are hydrogen, methyl, or fluoro being the same or different with the proviso that one of R$_{15}$ and R$_{16}$ is fluoro only when the other of R$_{15}$ and R$_{16}$ is hydrogen or fluoro;
wherein $$-\underset{\underset{L_1}{\|}}{C}-R_{17} \text{ taken together is}$$

(1) $-\underset{\underset{}{}}{\overset{CH_3}{CH}}-CH_2C\equiv C-CH_3,$ (2) —C≡C—C$_q$H$_{2q}$CH$_3$ wherein q is an integer of from 2 to 6, or
(3) —C$_p$H$_{2p}$CH=CH$_2$ wherein p is an integer of from 3 to 7; and pharmacologically acceptable salts and individual optical isomers thereof.

2. A compound of claim 1 wherein Y is —CH$_2$CH$_2$—, —C≡C— or trans—CH=CH$_2$.

3. A compound of claim 2 wherein Z$_4$ is —CH$_2$—.

4. A compound of claim 3 wherein Q is —COOR$_5$ or —COL$_2$ wherein L$_2$ is —NR$_9$R$_{10}$.

5. A compound of claim 4 wherein Q is —COOR$_5$ and $$-\underset{\underset{L_1}{\|}}{C}-R_{17} \text{ is } -\underset{\underset{H}{|}}{\overset{CH_3}{\underset{|}{C}}}-CH_2C\equiv CCH_3$$

6. A compound of claim 5 which is 9-deoxy-2',9α-methano-16-methyl-3-oxa-18,19-tetradehydro-4,5,6-trinor-3,7-(1',3'-interphenylene)-PGF$_1$.

7. A compound of claim 5 which is 9-deoxy-2',9α-methano-16-methyl-3-oxa-18,19-tetradehydro-4,5,6-trinor-3,7-(1',3'-interphenylene)-15-epi-PGF$_1$.

* * * * *